US00PP37644P2

(12) United States Plant Patent
Carrella

(10) Patent No.: US PP37,644 P2
(45) Date of Patent: Aug. 25, 2026

(54) ***LANTANA* PLANT NAMED 'KLELA24691'**

(50) Latin Name: *Lantana camara*
Varietal Denomination: KLELA24691

(71) Applicant: KLEMM + SOHN GMBH & CO. KG, Stuttgart (DE)

(72) Inventor: Angelo Carrella, Palma Campania (IT)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/260,359

(22) Filed: Jul. 4, 2025

(51) Int. Cl.
*A01H 5/02* (2018.01)
*A01H 6/86* (2018.01)

(52) U.S. Cl.
USPC ..... Plt./227
CPC ..... *A01H 6/86* (2018.05)

(58) Field of Classification Search
USPC ..... Plt./227
CPC ..... A01H 5/02
See application file for complete search history.

(56) References Cited

PUBLICATIONS https://www.lienhorticole.fr/en-direct/article/845016/lantana-camara-playa-sun-juana; Sep. 23, 2023; 3 pages.*
Chrome-extension://efaidnbmnnnibpcajpcglclefindmkaj/https://josvainiugeles.lt/wp-content/uploads/2024/09/Selecta-Annuals-2025.pdf; Jan. 1, 2024; 2 pages.*
https://www.linkedin.com/posts/andrea-piras-943702156_playa-sun-juana-lantana-camara-activity-7156301455535030273-2gd9; Approximately Oct. 31, 2024 (published 1 year ago which would be at least Oct. 31, 2024 as the internet search was done Oct. 31, 2025); 2 pages.*
In re Wingen; Feb. 2, 2023; 9 pages.*

* cited by examiner

*Primary Examiner* — Kent L Bell
(74) *Attorney, Agent, or Firm* — Weatherly IP Solutions, LLC; Karen P. Bechtold; James M. Weatherly

(57) ABSTRACT

A new *Lantana* plant particularly distinguished by having an excellent branching and mounding habit, a flower color that changes during flower development from orange buds to yellow-orange when the flower opens, and to bright magenta as the final color, and large flowers with continuous flowering from April through November, is disclosed.

1 Drawing Sheet

Genus and species: *Lantana camara.*
Variety denomination: 'KLELA24691'.

BACKGROUND OF THE NEW VARIETY

The present invention relates to a new and distinct cultivar of *Lantana* plant botanically known as *Lantana camara* and hereinafter referred to by the cultivar name 'KLELA24691'.

'KLELA24691' is the result of an open pollination of variety 'LA-2019-FV3605' (unpatented). The seeds were collected in July 2020 in Latina, Italy. The variety was selected in April 2021 in Latina, Italy and subsequently propagated by cuttings in Latina, Italy in April 2021. 'KLELA24691' has demonstrated that the new cultivar reproduces true to type with all of the characteristics, as herein described, firmly fixed and retained through successive generations of such asexual propagation.

SUMMARY

The following are the most outstanding and distinguishing characteristics of this new variety when grown under normal horticultural practices in Stuttgart, Germany.

1. Excellent branching and mounding habit;
2. Color changes during flower development from orange buds, to yellow orange when the flower opens, and to bright magenta as the final color;
3. Big flowers with continuous flowering from April to November.

DESCRIPTION OF THE PHOTOGRAPH

This new *Lantana* variety is illustrated by the accompanying photograph which shows a close-up of the whole plant. The photograph is of a 13-week-old-plant grown outdoors in Stuttgart, Germany in July 2022. The colors shown are as true as can be reasonably obtained by conventional photographic procedures.

DETAILED DESCRIPTION OF THE NEW VARIETY

The following detailed description and measurements were collected in June of 2025 and obtained from plants grown 20 weeks from transplant in Latina, Italy. The chart used in the identification of colors described herein is The R.H.S. Colour Chart of The Royal Horticultural Society, London, England, 5$^{th}$ edition (2007), except where general color terms of ordinary significance are used.

Classification:
*Family.*—Verbenaceae.
*Botanical.*—*Lantana camara.*

Parentage:
*Female parent.*—'LA-2019-FV3605' (unpatented).
*Male parent.*—Unknown.

Plant:
*Habit and general appearance.*—Mounding.
*Height* (*measured from the top of the soil*).—14.2 cm.
*Width* (*horizontal plant diameter*).—35.4 cm.

*Time to produce a finished plant.*—Approximately 10 to 12 weeks in warm greenhouse conditions and approximately 14 to 16 weeks in cold greenhouse conditions.
*Natural flowering season.*—Mid-spring to summer to till autumn, April to November.
*Time to initiate and develop roots.*—8 to 10 days.
*Root description and habit.*—Moderately dense and moderately branching white roots.
*Propagation type.*—Vegetative cuttings.
*Hardiness.*—Drought tolerance, heat resistance.

Lateral branches:
*Branching habit.*—Excellent branching, mounding habit.
*Quantity per plant.*—4 to 7 primary stems.
*Length.*—16.2 cm (average).
*Internode length.*—2.5 cm (average from stem base to top stem).
*Diameter (from midpoint).*—0.2 cm.
*Color, immature.*—RHS 144B.
*Color, mature.*—RHS 144B.
*Strength.*—Strong.
*Texture and luster.*—Pubescent, brilliant RHS N144B.
*Anthocyanin.*—Absent.

Leaves:
*Quantity of leaves per branch.*—10 to 16.
*Arrangement.*—Even pinnate.
*Length.*—3.6 cm to 7.1 cm.
*Width.*—2.1 cm to 4.5 cm.
*Shape.*—Ovate.
*Apex.*—Narrow acute.
*Base.*—Acute.
*Margin.*—Dentate.
*Texture and luster.*—Upper surface: Pubescent, RHS NN155A, darker. Lower surface: Pubescent, RHS NN155A, lighter than upper surface.
*Color, immature.*—Upper surface: RHS 138A. Mature surface: RHS 138D.
*Color, mature.*—Upper surface: RHS N137C. Lower surface: RHS 137D.
*Venation color.*—Upper surface: RHS N137C. Lower surface: RHS 144D.

Petiole:
*Color.*—Upper surface: RHS 144D. Lower surface: RHS 144D. Length: 1.0 cm. Diameter: 0.1 cm. Strength: Strong. Texture and luster: Pubescent, brilliant.

Inflorescence:
*Arrangement and habit.*—Mounded.
*Flower longevity on the plant.*—5 to 7 days.
*Type.*—Umbel.
*Quantity per plant.*—Approximately 30.
*Fragrance.*—Absent.
*Inflorescence diameter.*—4.9 cm.
*Inflorescence height.*—2.3 cm.
*Flower diameter.*—1.2 cm.
*Flower depth (height).*—1.9 cm including flower tube.
*Flower throat diameter (at base of petal lobes).*—0.2 cm.
*Flower tube length.*—1.5 cm.
*Flower tube diameter.*—0.15 cm (measured in the middle of tube).

Peduncle:
*Strength.*—Strong.
*Shape.*—Cylindrical.
*Aspect.*—Pubescent.
*Length.*—4.6 cm.
*Diameter.*—0.1 cm.
*Texture.*—Pubescent.
*Color.*—RHS 144B.

Flower description:
*Type.*—Inflorescence, rounded.

Bud:
*Shape.*—Rounded (flower disc).
*Color.*—RHS N30C (top of single flower in bud and first disc of flowers).
*Height.*—0.55 cm.
*Diameter.*—1.4 cm.

Petals:
*Arrangement.*—4 petals per flower, arranged in a single whorl.
*Upper petal.*—Length of upper petal from throat: 0.4 cm. Width of upper petal: 0.8 cm.
*Lateral petals.*—Length of lateral petals from throat: 0.45 cm. Width of lateral petals: 0.5 cm.
*Lower petal.*—Length of lower petal from throat: 0.7 cm. Width of lower petal: 0.9 cm.
*Lobe shape.*—Upper petal: Rounded. Lateral petal: Rounded. Lower petal: Oblong.
*Lobe apex.*—Rounded.
*Base.*—Rounded.
*Margin.*—Crenate.
*Texture and luster.*—Medium strong. Upper and lower surfaces: Upper, lateral and lower petals: Smooth.
*Color when opening.*—Upper surface: Upper, lateral and lower petals: RHS 14 B. Lower surface: Upper, lateral and lower petals: shaded RHS 13 A and RHS 12 C with anthocyanins parts RHS N74A.
*Color when fully opened.*—Upper surface: Upper, lateral and lower petals: RHS N71B. Lower surface: Upper, lateral and lower petals: RHS 70D.

Corolla tube:
*Length.*—1.5 cm.
*Diameter at midpoint.*—0.2 cm.
*Color.*—Inner surface: RHS 69B. Outer surface: RHS 69D.
*Texture and luster.*—Inner surface: Smooth, slightly glossy. Outer surface: Smooth, dull.

Calyx:
*Arrangement and quantity per flower.*—A single calyx tube per flower with 20 to 88 fused sepals, depending on the size of each inflorescence.
*Shape.*—Tubular.
*Sepals.*—Length: 0.4 cm. Width: 0.1 cm. Shape: Narrow acute. Apex: Acute. Base: Truncate. Margin: Serrate. Texture and luster: Upper surface: Pubescent, medium glossiness. Lower surface: Pubescent, medium glossiness. Color: Upper surface: RHS N144C. Lower surface: RHS 145C.

Bracts:
*Quantity per flower.*—1 for each flower in the inflorescence.
*Shape.*—Lanceolate.
*Length.*—0.8 cm.
*Width.*—0.1 cm.
*Texture of upper and lower surface.*—Pubescent, both.
*Color of upper and lower surfaces.*—RHS 144B.

Reproductive organs:
*Stamens.*—Quantity per flower and arrangement: 4 per flower, adnate to floral tube.
*Filament.*—Length: 0.6 cm. Color: RHS 158C.
*Anther.*—Length: 0.1 cm. Shape: Oblong. Color: RHS 6C. Pollen amount: Low to medium quantity. Pollen color: RHS 6B.
*Pistils.*—Quantity per flower: 1. Length: 0.4 cm.
*Stigma.*—Diameter: Less than 0.1 cm. Shape: Rounded. Color: RHS 144D.

*Style*.—Length: 0.4 cm. Color: RHS 144D.

*Ovary*.—Width: Less than 0.1 cm. Shape: Rounded. Color: RHS 144D.

Seed and fruit production: Not observed.

Disease and pest resistance: Not observed.

COMPARISON OF 'KLELA24691' WITH PARENTAL LINE AND KNOWN VARIETY

'KLELA24691' is distinguished from the parental line as described in Table 1.

TABLE 1

| Comparison with Parental Line | | |
|---|---|---|
| Trait | Variety 'KLELA24691' | Female parent 'LA-2019-FV3605' |
| Branching | Excellent branching | Medium branching |
| Vigor | Medium vigor | More vigor than 'KLELA24691' |

'KLELA24691' can be compared to the commercial *Lantana* variety 'Bandana Hot Pink' (unpatented). Differences between the varieties are described in Table 2.

TABLE 2

| Comparison with Similar Variety | | |
|---|---|---|
| Trait | 'KLELA24691' | 'Bandana Hot Pink' |
| Main flower color | Magenta color | Pink color |
| Vigor | Medium vigor | vigorous |

The invention claimed is:

1. A new and distinct variety of *Lantana* plant as shown and described herein.

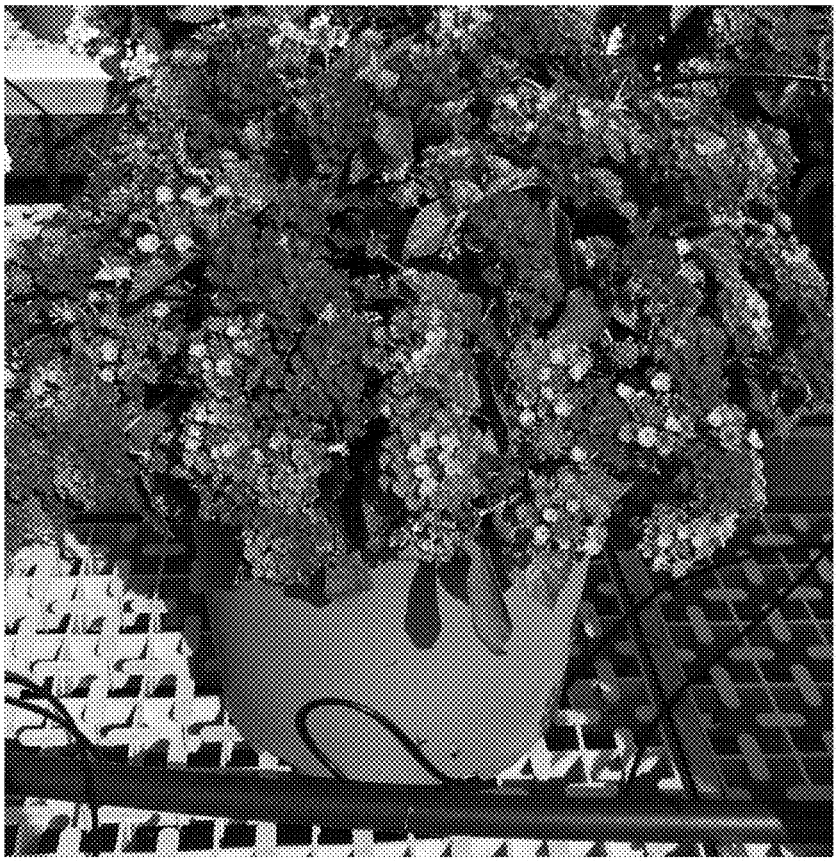

* * * * *